(12) United States Patent
Agah et al.

(10) Patent No.: US 10,048,222 B2
(45) Date of Patent: Aug. 14, 2018

(54) MINIATURIZED HELIUM PHOTOIONIZATION DETECTOR

(71) Applicants: Masoud Agah, Blacksburg, VA (US); Shree Narayanan Sreedharan Nair, Hillsboro, OR (US)

(72) Inventors: Masoud Agah, Blacksburg, VA (US); Shree Narayanan Sreedharan Nair, Hillsboro, OR (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 43 days.

(21) Appl. No.: 14/529,760

(22) Filed: Oct. 31, 2014

(65) Prior Publication Data
US 2015/0130473 A1    May 14, 2015

Related U.S. Application Data

(60) Provisional application No. 61/898,861, filed on Nov. 1, 2013.

(51) Int. Cl.
  *G01N 27/66* (2006.01)
  *G01N 27/68* (2006.01)
(52) U.S. Cl.
  CPC .................. *G01N 27/68* (2013.01)
(58) Field of Classification Search
  CPC ................. G01N 27/66; G01N 27/64
  USPC .................................................. 324/464
  See application file for complete search history.

(56) References Cited

U.S. PATENT DOCUMENTS

| | | | | |
|---|---|---|---|---|
| 5,394,092 A | * | 2/1995 | Wentworth | G01N 27/70 324/455 |
| 6,236,213 B1 | * | 5/2001 | Maruta | F02P 17/12 324/393 |
| 6,448,777 B1 | * | 9/2002 | Abdel-Rahman | G01N 27/70 324/464 |
| 7,100,421 B1 | * | 9/2006 | Herring | G01N 30/64 324/464 |
| 7,812,614 B2 | * | 10/2010 | Kurita | G01N 27/64 324/464 |
| 8,963,554 B2 | * | 2/2015 | Stearns | G01N 30/64 324/122 |
| 2004/0108857 A1 | * | 6/2004 | Jarski | G01N 27/62 324/464 |
| 2005/0147992 A1 | * | 7/2005 | Quake | B01L 3/5027 435/6.1 |
| 2007/0158548 A1 | * | 7/2007 | Haigh | G01N 27/622 250/287 |
| 2008/0160732 A1 | * | 7/2008 | Barthelmess | H01L 21/263 438/528 |

(Continued)

*Primary Examiner* — Son Le
*Assistant Examiner* — Akm Zakaria
(74) *Attorney, Agent, or Firm* — Keith A. Vogt; Vogt IP

(57) ABSTRACT

The present invention provides an ionization detector having a base having an enclosed chamber. The enclosed chamber has a first end and a second end. The detector also includes a first outlet which is a source of an excitable medium. A second outlet is provided which functions a source of an analyte that is transported by a carrier gas. An ionization source for creating a discharge from said excitable medium is also provided. The collector electrode generates a time dependent current based on its interaction with ionized analytes from which the analyte may be detected.

20 Claims, 7 Drawing Sheets

(56) References Cited

U.S. PATENT DOCUMENTS

2012/0286154 A1* 11/2012 Zimmermann ........ G01N 30/12
                                                              250/282

* cited by examiner

MINIATURIZED HELIUM PHOTOIONIZATION DETECTOR

RELATED APPLICATIONS

This application claims the benefit of U.S. Provisional Application No. 61/898,861, filed Nov. 1, 2013.

STATEMENT REGARDING FEDERALLY SPONSORED RESEARCH & DEVELOPMENT

This invention was made with government support under Grant No. ECCS0747600 awarded by the National Science Foundation and Grant No. R21_OH010330 awarded by the Centers for Disease Control and Prevention. The government has certain rights in the invention.

INCORPORATION BY REFERENCE OF MATERIAL SUBMITTED ON A COMPACT DISC

Not applicable.

BACKGROUND OF THE INVENTION

Micro gas chromatography (µGC) is based on developing miniaturized, portable systems capable of identifying the composition of a gas mixture by separation into its individual components and are applicable for homeland security, space exploration, on-site or distributed environmental monitoring mechanisms, and food assessment. In a typical µGC system, the sample mixture is first collected on an adsorbent bed referred to as the pre-concentrator. When thermally spiked, this device releases the adsorbed species in a sharp vaporized plug. This narrow plug enters a microfluidic channel, called the separation column, which is coated with a stationary phase film to chemically interact and retard the various analytes of the plug to different extents. The analytes are then separated in time and, ideally, elute out of the column one-by-one into a detector. An inert carrier gas (mobile phase) such as helium or nitrogen facilitates the movement of the analytes through the entire system.

Miniaturization offers unique advantages such as lightweight, low power consumption, less reagent usage and innovative architectures apart from lower cost when batch fabricated. Stereotypical miniaturization utilizes components fabricated in silicon/glass. Common implementations involve etching a narrow bore microfluidic channel in silicon/glass wafers, with capillary dimensions similar to conventional GC columns, or fabricating posts within the silicon cavity and coating with an adsorbent material. The primary incentive is the ability to conveniently pack a 1-2 m length tubing (cavity) into a 2 cm×4 cm×500 µm silicon die without having to wind equivalent length capillary tubing into a large coil. In addition, heating a silicon die with on-chip heaters is energetically far less taxing compared to heating capillary tubing with a convection oven.

The choices for detectors in the micro-world are numerous. While traditional GC systems are dominated by flame ionization detectors (FID), electron capture detectors (ECD) and flame photometric detectors (FPD), µGC offers the possibility of obtaining signals via other forms of reactive processes using sorptive sensors that transduce into electrical, acoustic or optical domains. In general, any concentration-sensitive detector, such as the thermal conductivity detector (TCD), are more pliable to be reduced in size. It should be noted that while ionization detectors such as the FID provide robust performance and sensitivity, efforts to miniaturize them do not yield comparable detection levels since the hydrogen flame loses its ionizing potential when reduced in size. On the other hand, sorptive and thermal sensing detectors have inherent limitations since they are more temperature sensitive and hence their implementation and application has been inadequate as well. Mass spectrometry (MS), considered the gold standard in conventional analytical techniques, has also been subject to miniaturization. A majority of these efforts have focused on reducing the size of a MS using techniques that are not found in silicon micromachining. This has resulted in dimensions slightly larger than that found in µGC and a power dissipation on the order of tens of watts.

Commercially available µGC systems have adopted a hybrid approach wherein the detector is similar in style to conventional ultraviolet photoionization detectors (UV-PID). These systems offer excellent detection sensitivity, but are somewhat restricted by the photoionization energies available (<11.7 eV with argon lamps) as well as incorporation into a µGC system.

Micro-discharges or plasmas have also been utilized in gas detectors. One such detector uses fragmented analytes in a DC microplasma to produce diatomic fragments from which emission are detected spectrophotometrically. Improvements on this technique included an innovative electrode structure to generate a pulsed plasma with drastically reduced power consumption.

However, spectrophotometric detection is an intensive operation that consumes power on the order of watts. An alternative is to monitor the current through the discharge itself. However, a common concern with these designs is the fouling of the electrodes due to fragmentation of the analytes. Fragmentation also does not allow for the analytes to be subjected to further analysis.

BRIEF SUMMARY OF THE INVENTION

Unlike the above-described devices, some embodiments of the present invention provide a sensitive, low-power, easy-to-fabricate universal detector that utilizes a microdischarge. The embodiments utilize high-energy photons and excited state helium metastable species to ionize the analytes. The resultant current is monitored on a remote sensing or collector electrode.

Other embodiments provide a sensor that is insensitive to temperature, which makes them suitable for robust gas detection system. In other embodiments, injected quantity and concentration of the analytes is varied to produce a device with a 350 pg limit of detection (LOD).

In other embodiments, the response of the detector is directly related to the discharge voltage of the carrier gas, bias electrode-to-discharge distance, collector-to-bias distance, and bias voltage. In some embodiments that utilize optimized parameters, an absolute limit of detection of 60 pg for octane in air at 3.3 mW is obtained.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Figure 1A:
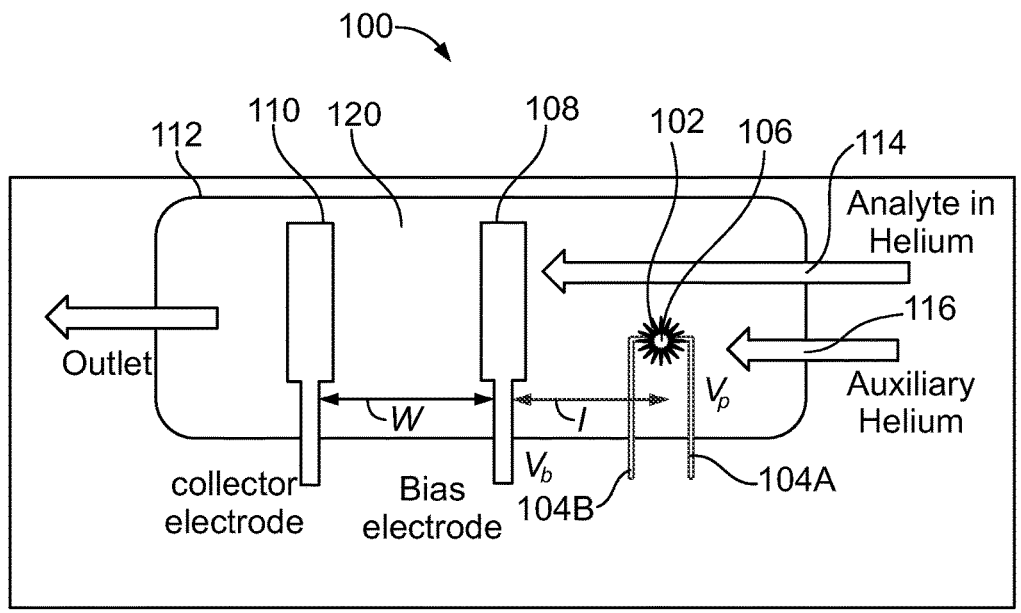
FIG. 1A is a schematic diagram showing one embodiment of the present invention.
Figure 1B:
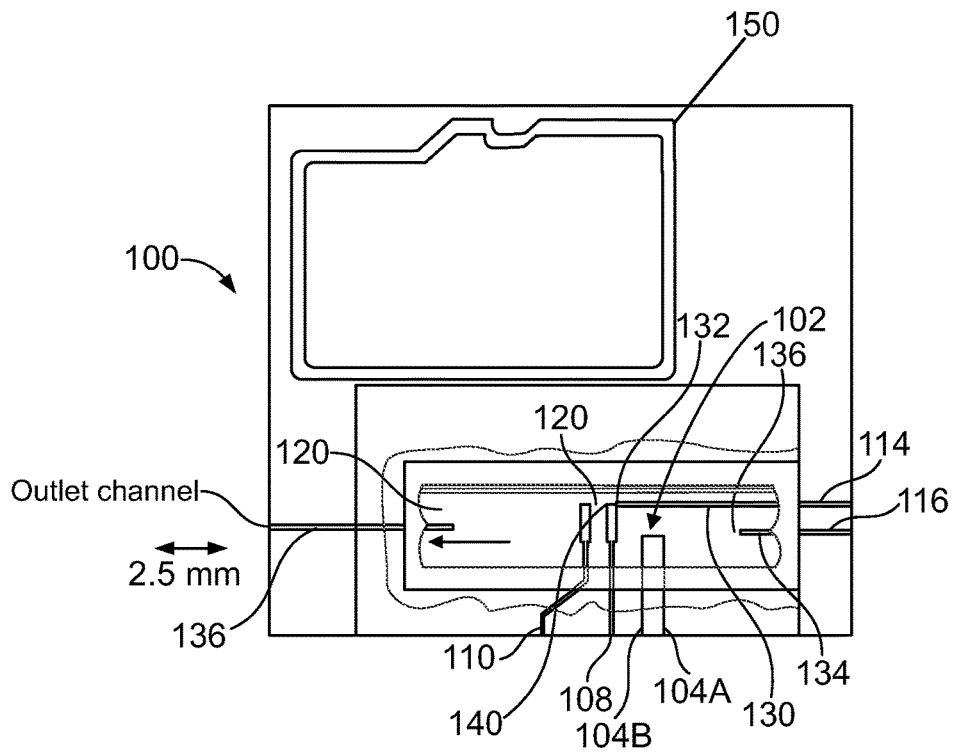
FIG. 1B is top view of a detector assembly with portions removed to illustrate components of the detector.

As shown in FIGS. 1A and 1B, some embodiments of the present invention provide a micro-helium discharge ionization detector (μHDID) 100 that is an ionization style detector that operates by measuring the resultant current from the ionization of the analytes without molecular fragmentation. Detector 100 utilizes a high voltage DC discharge gap 102 created by spaced-apart electrode pair 104A and 104B. The gap may be a distance of 20 μm and other distances as described below. As also shown in FIG. 1A, the parameters of interest, namely l, w, $V_p$, and $V_b$ are denoted.

When voltage is applied across gap 102, a spark is generated that excites an excitable medium, which acts as a source of high-energy photons and metastable excited atoms to generate micro-discharge 106. Discharge 106 is used to ionize an analyte. A preferred excitable medium is Helium (He), which is thought to be the dominant species responsible for the ionization of the analyte species. In addition, other gasses may be used as the source of the excitable material as known to those of skill in the art.

As further shown in FIGS. 1A and 1B, the device also consists of a bias electrode 108 and a sensing or collector electrode 110 which may be thin films as known to those of skill in the art. Electrode 110 is a spaced distance from electrode 108 to form a predetermined volume 120, which influences the level of signal response generated. The excitable medium is introduced via port 116 and flows through channel 134 and is discharged at outlet 136. Outlet 136 may be in a spaced-apart relationship with respect to gap 102. The analytes are introduced to the system via port 114 and channel 130. The analyte is carried by the excitable medium through channel 130 and discharged by outlet 136. Outlet 136 is in close proximity to terminal end 140 of bias electrode 108. It has been found that this location provides optimal performance. However, outlet 136 may be located in collector volume 120. Another preferred location is to locate outlet 136 between the ionization source, such as electrodes 104A and 104B, and electrode 110. All components may be contained in a chamber or channel 112 of device 100.

When the excitable medium is suitably excited, the resulting discharge 106 results in the generation of a complex mix of positive and negatively charged ions, metastable atoms, electrons, and photons. These omnidirectional energetic particles constitute an ionizing flux of discharge 106. Some of these particles, such as metastable atoms and ions, flow downstream due to pressure-driven flow. Thus, the ionizing flux at bias electrode 108 is a mix of positive and negatively charged particles as well as high-energy photons and metastable atoms. In a preferred embodiment, the excitable medium may be He and the high-energy components of the resulting discharge or ionizing flux (normally considered to be photons with energies >10 eV and metastable He atoms with energies of 19.8 eV) are responsible for ionization of an analyte species. The transmission of this flux through the detector volume decays exponentially due to absorption, and is given by $$I_b = I_0 e^{-\alpha l} \quad (1)$$

$I_b$, the flux observed at bias electrode 108, is related to the initial discharge emission $I_0$ by Beer-Lambert's law for photon flux transmission. α is the absorption coefficient of helium over the length of the detector (l) from the He discharge to the bias electrode. In some embodiments, l may be minimized to increase the flux density available at bias electrode 108. In other embodiments, gap 102 width w should be maximized to increase the total flux available for the analyte species within the collector volume 120 where the photon flux needs to be absorbed to the maximum extent. However, recombination processes with electrons within this volume can cause a portion of the generated carriers to be neutralized and hence not detected. The net effect of these factors determines the distance between electrodes 108 and 110 in which a generated charge carrier will result in a favorable current. In the presence of a bias voltage, the effect of an electric field between closely spaced bias electrode 108 and collector electrode 110 can be advantageous in isolating the generated carriers within the collector volume more efficiently. The lifetime of metastable He species available for collisional energy transfer to analyte species will be a factor as well. A number of these factors are considered in the following discussion.

In some preferred embodiments, detector 100 may be fabricated from borosilicate glass wafers. Other substrate materials may also be used. In a preferred embodiment, wafers 700 μm in thickness and 100 mm in diameter were used as substrate wafers for fabrication of the microplasma devices of the present invention. In other embodiments, separation columns may be used with the present invention and may be prepared from 100 mm <100> silicon wafers of 500 μm thickness.

Figure 2A:
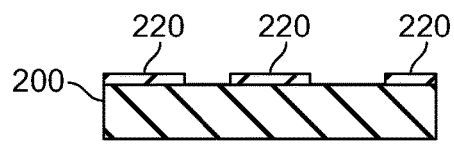
FIGS. 2A-2D show a preferred embodiment of a patterning process used to create a detector in accordance with one embodiment of the present invention.
Figure 2B:
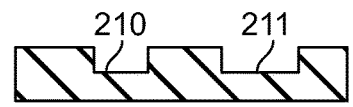
Figure 2C:
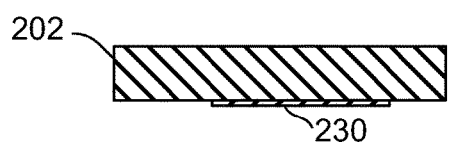
Figure 2D:
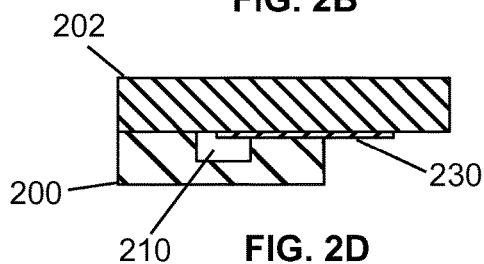

As shown in FIGS. 2A-2D, detector 100 may be constructed from two Borofloat wafers 200 and 202. To fabricate microfluidic channels 210 and 211, wafer 200 was blanket deposited with 50 nm/30 nm chromium/gold by e-beam physical vapor deposition (PVD-250, Kurt Lesker). Photoresist 220 (AZ9260) was spun-coated and lithographically patterned with a first mask, to create fluidic channels 210 and 211 as well as bond pads. After etching the chromium and gold layers, the Borofloat was deep etched to a depth of 260 μm using a 10:1 HF/HCl mixture as shown in FIG. 2A. As shown in FIG. 2B, wet etching and stripping are next performed. The top Borofloat wafer 202 was spun-coated with AZ9260 and patterned. A 1 μm/25 nm titanium/gold stack 230 was e-beam deposited and patterned by lift-off to form the electrodes as shown in FIG. 2C. Both wafers were diced into individual devices and bonded together with epoxy as shown in FIG. 2D. Capillary tubing of 100 μm I.D. and 200 μm O.D., which may be used to form channels 130 and 134, were slid into the exits and sealed. FIG. 1B illustrates a completed assembly 100.

Figure 3:
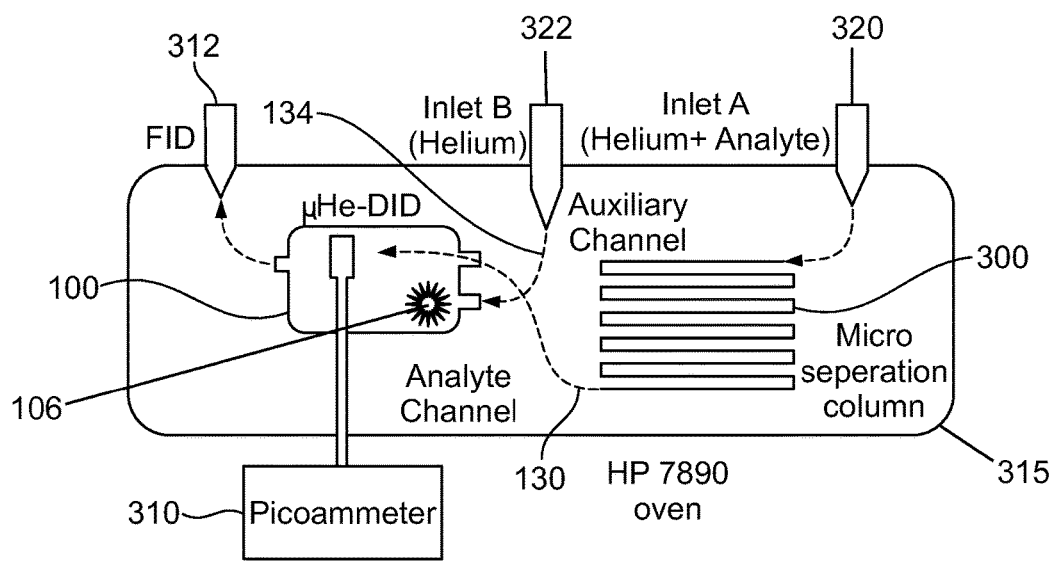
FIG. 3 illustrates a detector assembly of an embodiment of the present invention.

As shown in FIG. 3, a 80 μm-wide, 240 μm-deep and 1 m-long micromachined separation column 300 is also provided which may be intergrated into detector 100 or be a separate unit that is connected to detector 100. Column 300 may be fabricated using standard processes known to those of skill in the art to preform separations of analytes such as octane separations. FIG. 3 also shows a setup depicting the connections of detector 100. The auxiliary channel 134 feeds an excitable medium such as helium for microdischarge 106. The analyte channel 130 introduces the analytes from separation column 300, bypassing microdischarge 106. A picoammeter 310 reads the signal from the collector electrode. A FID 312 may be used for verifying the consistency of the injection.

To characterize the different embodiments of the present invention, a headspace of a 1.8 mL autosampler vial was filled with about 120 μL of reagent grade n-octane, which served as the source for constant vapor phase concentrations for gas-phase injections. To determine the limit-of-detection (LOD) for the embodiments, 25 to 200 μL of analytical grade n-octane were pipetted into a custom-made 1 L volumetric flask. The mouth of the flask was sealed with a 24/40 septa and left overnight for the octane to volatilize. To prepare different dilutions, the octane in the flask was cleared by removing the septa seal and running the flask through a cycle of nitrogen purging, oven heating at 80° C., and repurging with nitrogen. After letting the flask cool down to room temperature, the volume of octane corresponding to the desired concentration was pipetted into the flask, which was then re-sealed and left to homogenize.

Table 1 provides a listing of various embodiments of the present invention and their design parameters. Devices within design parameter sets 1-3 were fabricated with a fixed bias electrode 108 to collector electrode 110 distance (w=2.5 mm) but vary with the distance of the bias electrode 108 from discharge 106 (l). Devices within design parameter sets 4-6 have the bias electrode 108 at a fixed distance from discharge 106 (l=1.5 mm) but vary in the distance of collector electrode 110 from bias electrode 108 (w). The third column provides the distance from the midpoint between the collector electrode 110 and bias electrode 108 to discharge 106. Its significance will be discussed in a later section.

TABLE 1

Six different designs with values for the parameters l (distance between the He discharge and bias electrode) and w (distance between the bias and collector electrode). The distance from He discharge to the midpoint of the gap between the electrodes is calculated in the fourth column from the previous two. Multiple devices of the same design were tested in most cases.

| Design # | Length l (mm) | Gap width w (mm) | Discharge to gap midpoint (l + w/2), (mm) |
| --- | --- | --- | --- |
| 1 | 5 | 2.5 | 6.25 |
| 2 | 3 | 2.5 | 4.25 |
| 3 | 1.5 | 2.5 | 2.75 |
| 4 | 1.5 | 1 | 2 |
| 5 | 1.5 | 2 | 2.5 |
| 6 | 1.5 | 3 | 3 |

As shown in FIG. 3, a gas chromatography oven 315 was fitted with two electronic pressure control (EPC) inlets 320 and 322 and FID 312 was used to test detector 100. An autosampler was fixed to inlet 320 when automated injections were required. The automated injection was configured for two sample priming events followed by drawing 1 μl from the 1.8 ml autosampler vials, all at a depth of 10 mm, to ensure consistent gas phase injections. A gas tight syringe was used for making manual injections of samples during LOD testing. Ultra high purity helium was used as the carrier and auxiliary gases. Industrial grade air and hydrogen generated by a hydrogen generator provided FID 312 gas supplies.

One end of separation column 300 was connected to inlet 320 and held at 96.5 kPa. The split flow on this inlet was set to allow 1/150 of the sample volume injected to reach the column. The other end of the column was connected to analyte channel 130 of detector 100. Analyte channel 130 bypasses discharge 106, which was fed by a helium flow from inlet 322 at 27.6 kPa, resulting in a 0.22 mL/min flow rate through auxiliary channel 134.

Both injection inlets 320 and 322 as well as FID 312 were maintained at 280° C. whereas detector 100 was maintained at ambient temperature. A picoammeter 310 was used to detect the signal from remote collector electrode 110 while a LabVIEW program recorded the measurement from the rear-terminal output via a digital multimeter. High voltage power supplies were used to provide the voltage necessary for the He discharge as well as the bias electrode voltage.

Plasma 106 was first characterized by exposing an uncapped-device to ambient air. For the IV-curve extraction shown in FIG. 4, a 100 MΩ resistor and a 10 MΩ resistor were connected in series with the excitation electrodes 104A and 104B exposed to air, and observed under a microscope.

Figure 4:
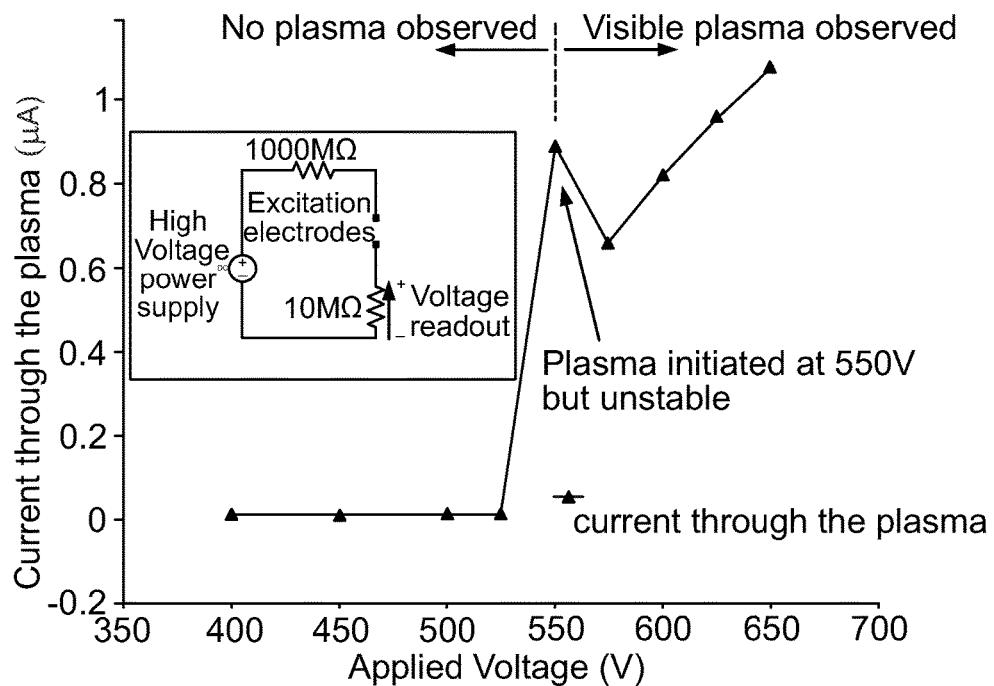
FIG. 4 depicts current through the plasma as a function of the applied voltage with the circuit used for the IV curve extraction shown in the inset for an embodiment of the present invention.

A high voltage power supply sources the "applied voltage" which is stepped up in increments. A Keithley 2700 DMM was used to measure the voltage across the 10 MΩ resistor. The current through the plasma was deduced from the voltage across the 10 MΩ resistor and plotted as shown in FIG. 4. For 525V and lesser, the current measured was on the order of tens of nanoamperes. At 550V an unstable plasma was observed with the current changing anywhere between tens of nanoamperes and a microampere.

Paschen's law relates the breakdown voltage across a gap as a function of the product of distance (d) across the gap and the pressure (p).

$$V = \frac{apd}{\ln(pd) + b}$$

Here, the empirically derived values for a and b are $4.36 \times 107$ V/(atm·m) and 12.8, respectively. Correspondingly, for p=1 atm and d=20×10-6 m in air, the breakdown voltage is deduced to be 440V. It should be noted that this voltage is strongly dependent on the electrode material, substrate and pressure, thus the deviation in the measured breakdown voltage can be attributed to this variation. However, for an applied voltage of 575V and higher, the current is found to roughly increase linearly with the applied voltage. The dynamic resistance within this section is calculated to be 68.6 MΩ.

For results reported hereafter, a 550 V DC potential was applied through a 50 MΩ resistor, across discharge electrodes 104A and 104B with bias electrode 108 grounded, and the current from collector electrode 110 recorded through picoammeter 310. This ensured a steady discharge across gap 102.

Figure 5:
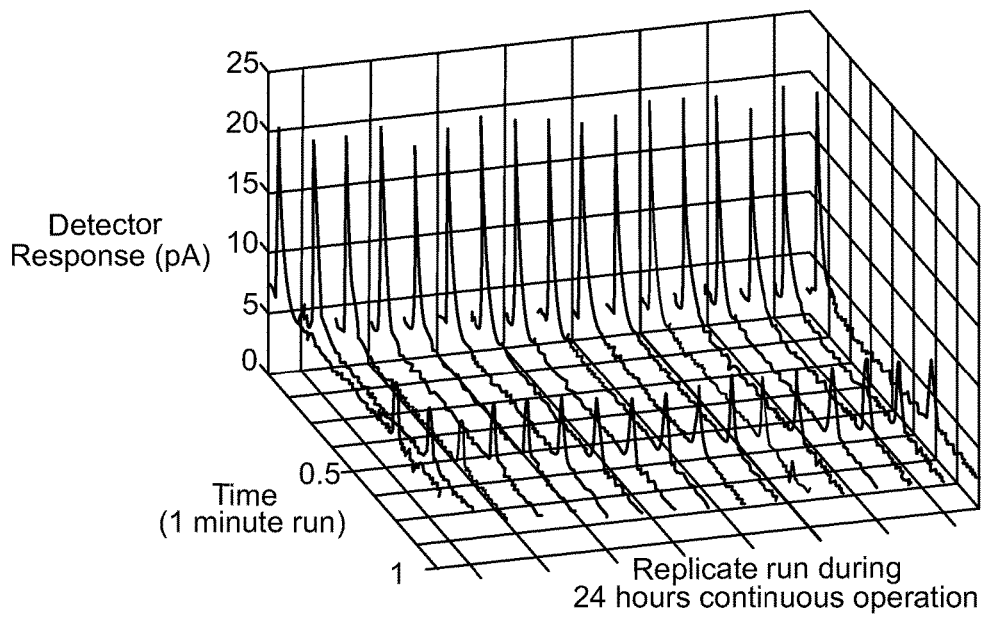
FIG. 5 is a series of chromatographic runs from injections of octane vapor in an autosampler vial headspace as detected fir an embodiment of the present invention.
Figure 6:
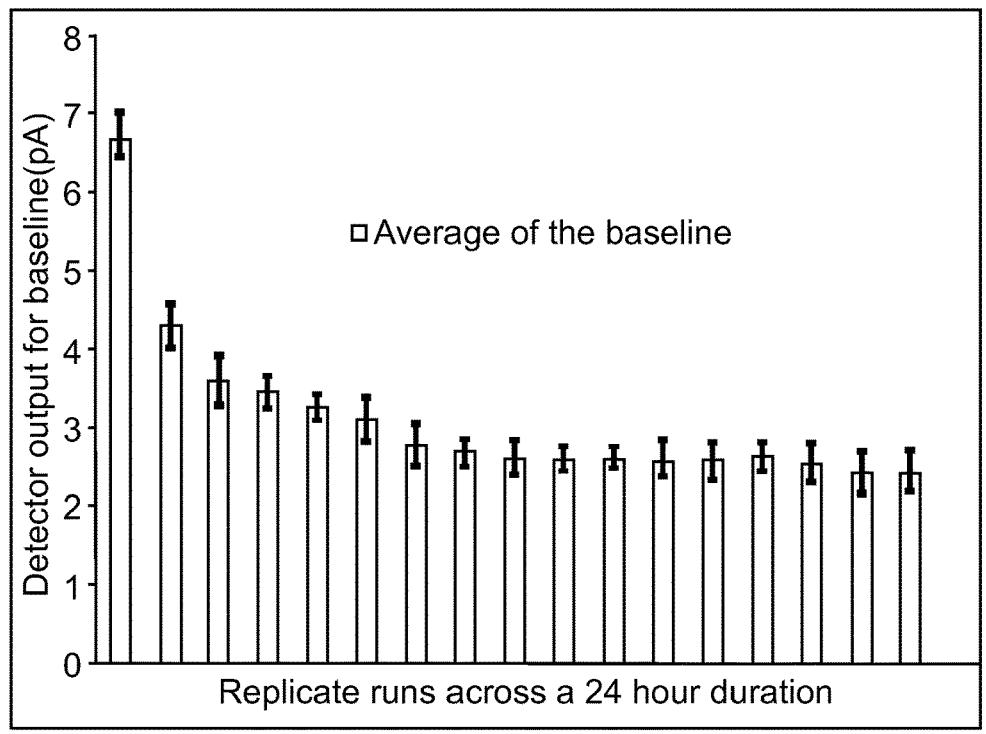
FIG. 6 is a plot of the average baseline obtained over a 24 hour period with the error bars indicating the variation in the baseline (noise) for each chromatographic run for an embodiment of the present invention.

To empirically study the impact of the signals generated over long time intervals, a 1 μL headspace of octane was injected from an autosampler every 1.5 hours over 24 hours of continuous operation and the response of the detector (via the picoammeter) recorded. FIG. 5 shows a stacked plot of the recordings with the earliest recording to the left. The raw data was smoothed with a 5-point moving average. The first peak corresponds to air, while the smaller peak that elutes at about 0.7 minutes corresponds to octane. The baseline for the detector decreases from its initial value by about 50% to eventually stabilize within 4 hours as shown in FIG. 6. This "burn-in" period was noticed in the first few hours of every detector and could correspond to the sputtering off of gold from the electrodes used to produce the discharge as well as removal of contaminant compounds used in the fabrication process. The burn-in process is not required every time the detector is operated, it is only necessary after initial fabrication of the detector. Thereafter, the baseline was observed to be relatively stable and the detector's response (peak height minus baseline) considered reasonably constant for measurements.

Figure 7:
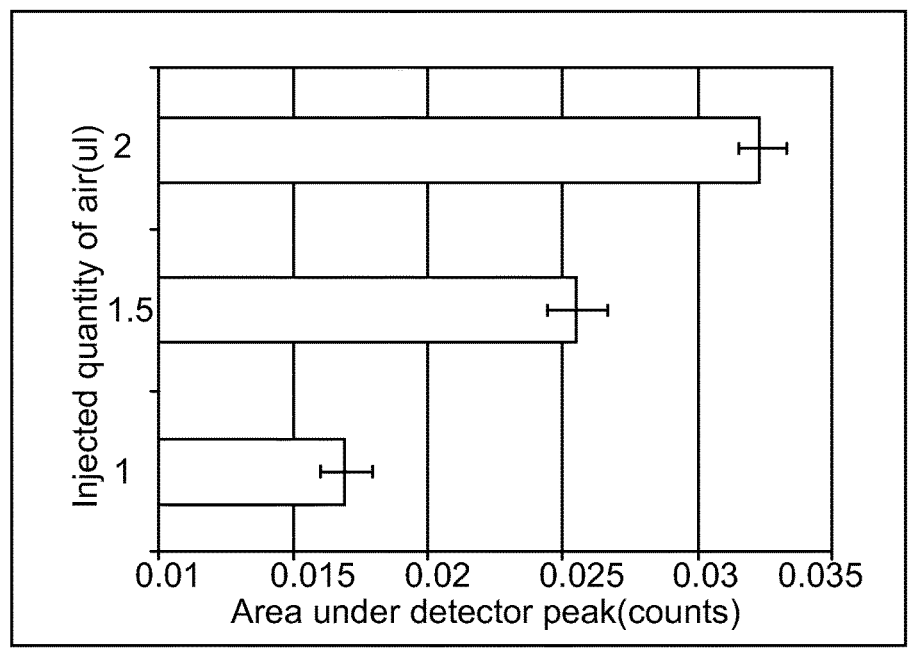
FIG. 7 shows the variation in detector response with injected quantity of air for an embodiment of the present invention.

Various quantities of air were injected into separation column 300 using the setup shown in FIG. 3, and the corresponding peak on the detector recorded. Air is not retained on the polydimethylsiloxane stationary phase and hence elutes in a few seconds. The corresponding peak is integrated to obtain a count, which is plotted in FIG. 7 against the amount injected. Apart from the universality of detector 100, this plot shows a dependence on the injected quantity of sample, which is a characteristic of a MSD.

Figure 8:
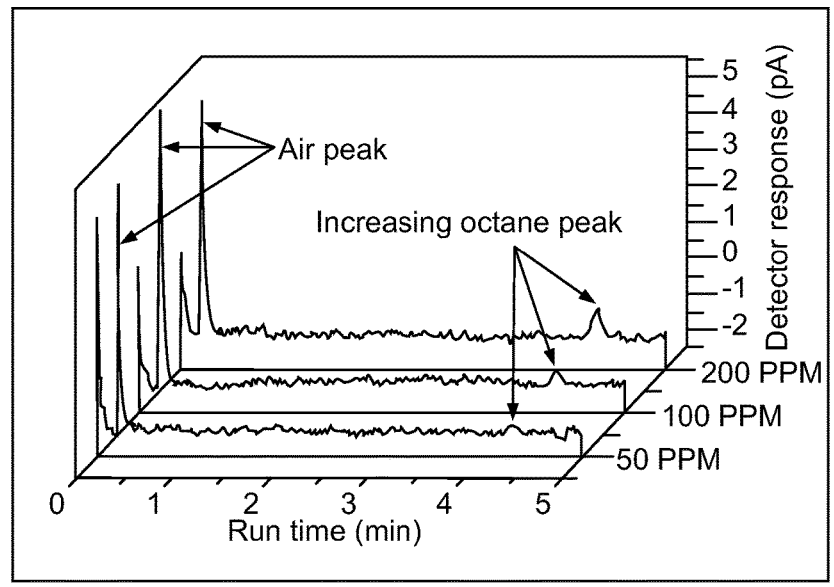
FIG. 8 is a comparative plot of 1 μl injections of 50, 100 and 200 ppm concentrations (volume/volume) of octane in air for an embodiment of the present invention.

The detector response was also determined as a function of the concentration of octane in air at 50, 100, and 200 ppm concentrations prepared as described. A 1 μl sample volume was injected into separation column 300 with the split ratio set to 1/100 on the HP5890 injector and an oven temperature of 20° C. Comparisons of the signals obtained are shown in FIG. 8. A 15-point moving average filter was used to smooth the high-frequency noise. The signal-to-noise-ratios (SNR) were calculated to be 3.4, 8.1 and 13.2 respectively. Thus, the demonstrated Limit of Detection (LOD) for this detector, with bias electrode 108 grounded, is approximately 50 ppm for octane, which translates to an absolute mass of approximately 350 pg.

Figure 9:
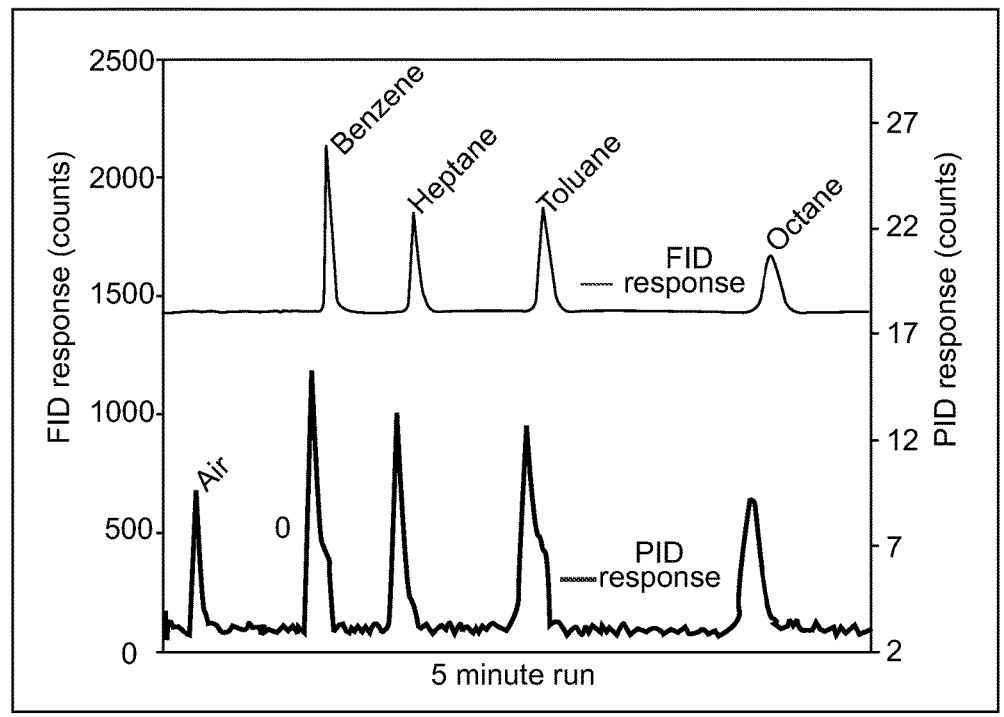
FIG. 9 shows the chromatogram of a 2 μl sample of 4-component mixture of benzene, heptane, toluene and octane in air for an embodiment of the present invention.

A 1 μl sample from a headspace mixture of benzene, heptane, toluene and octane, prepared as mentioned, was drawn into the syringe with an additional 1 μl of ambient air, resulting in the injection of a 2 μl volume into separation column 300. FIG. 9 is a chromatogram of the eluted components as detected by detector 100 and FID 312. The outlet capillary tube that follows detector 100 and connects it to the FID introduces a delay, accounting for the increased retention times in the FID. The universality of detector 100 is exemplified in that air in the sample is detected. Aromatics and aliphatic compounds are also detected with a similar response to the FID.

Multiple detectors of three different designs (Design 1, 2, and 3 in Table 1) were fabricated with a fixed distance between bias electrode 108 and collector electrode 110 at 2.5 mm, and varying distances between the bias electrode 108 and discharge 106. A total of 6 different detectors were tested (two of each of the three designs). The response of the detectors to 1 μl injections of octane in the headspace of autosampler vials was measured with excitation voltages from 550 V to 700 V in increments of 50 V used to produce the He discharge, with the bias electrode grounded. The peak height corresponding to octane for the range of discharge voltages is plotted in FIG. 10 for each design. Three tests were performed at every voltage for each of the 6 detectors, two of each design, and the peak heights averaged. The error bar represents the standard deviation in the multiple measurements. The positive slope on each line plot indicates that an increased voltage ($V_p$) predictably results in an enhanced response. This can be correlated to a larger current flux within the discharge gap, which produces a larger ionizing flux. This would be reflected in an increase in the value of $I_0$ in Equation 1.

Figure 10:
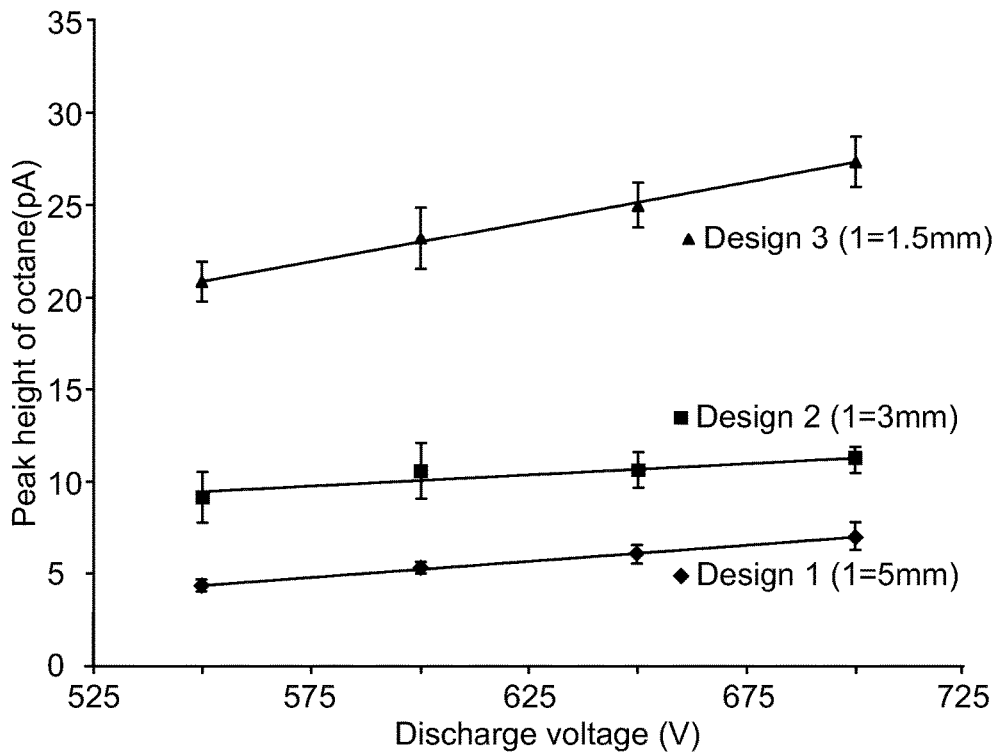
FIG. 10 shows the variation in the detector response to octane headspace injection at different discharge voltages for several different embodiments of the present invention.

The octane signal was also observed to increase significantly in FIG. 10 for smaller values of l. As the distance between discharge 106 and bias electrode 108 is decreased, the flux observed at the bias electrode increases. This effect can be correlated to the exponential term in Equation 1, and correspondingly results in better analyte ionization. In addition, the number of high energy photons and metastable He atoms available for analyte ionization should be enhanced by reducing the distance between discharge 106 and capillary outlet 132 directly above bias electrode 108, effectively improving the density of the ionizing flux at the capillary outlet. Thus, it can be concluded that for a given w, the detector with the smallest value for l gives a better response. The extent to which l can be minimized is limited by the possibility of fragmentation of the analyte upon introduction at the bias electrode and subsequent back-diffusion.

Figure 11:
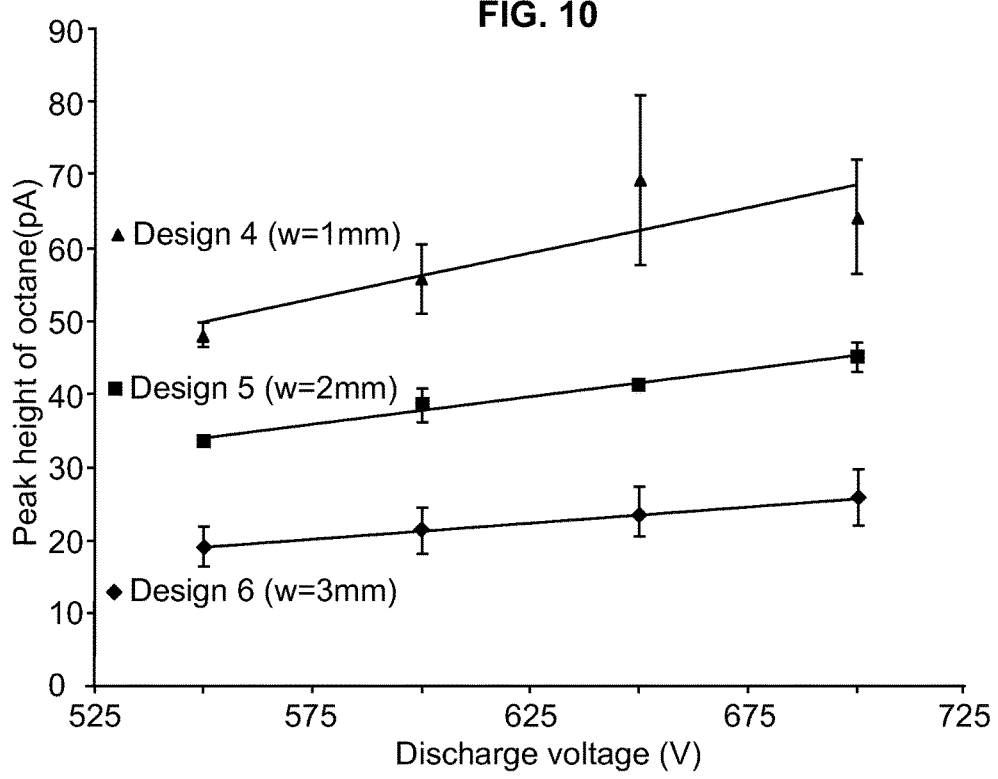
FIG. 11 shows the variation in the detector response to octane headspace injection at different discharge voltages for different embodiments with variations in the bias to collector electrode distance (w) and with a constant l=1.5 mm for an embodiment of the present invention.

Multiple detectors of three different designs (Design 4, 5, and 6) were fabricated and tested with the location of bias electrode 108 from He discharge 106 set at 1.5 mm. However, the distance of collector electrode 110 from bias electrode 108 was varied to understand the competing effects of ionization and recombination within collector volume 120. Plots for the detector response for the three designs over the same range of discharge voltages are shown in FIG. 11. Each data point is the average of triplicate runs performed on each detector at each voltage, from a total of 5 detectors. The error bars represent the standard deviation of the values for which the average is plotted. In a manner similar to the distance between the bias electrode and He discharge, signals were observed to increase as the distance between collector electrode 110 and bias electrode 108 decreased. The signal collected at collector electrode 110 relies on the ionization of analytes from the He discharge source to produce charged species with a sufficient lifetime to reach the collector electrode via the helium flow through the device. As this gap decreases, the time available for recombination effects, or neutralization of the charged species, decreases as well. Thus, for a given l, decreasing the width w is favorable.

The results from the previous two examples can be combined to obtain a simple relation for the detector response R (peak height of the octane signal) in terms of the length l and width w, $$R \propto V_p e^{-\alpha l}(1-\beta w) \qquad (2)$$

Here, $\alpha$ is the absorption coefficient from Beer-Lambert's law. $\beta$ is an empirical coefficient to account for the improved collection as the collector is brought closer to the bias electrode and can be related to the presence of a first order recombination/decay length constant. Using the slopes generated from the data plotted in FIGS. 10 and 11, the values of $\alpha$ and $\beta$ were estimated to be 0.45 $mm^{-1}$ and 0.23 $mm^{-1}$, respectively, at 550 V. The larger the value of $\alpha$, the quicker the decay of the flux from the He discharge and hence, the closer the bias electrode has to be positioned to the He discharge. On the other hand, a lower value of $\beta$ makes the design less sensitive to the width of the gap (w).

Figure 12:
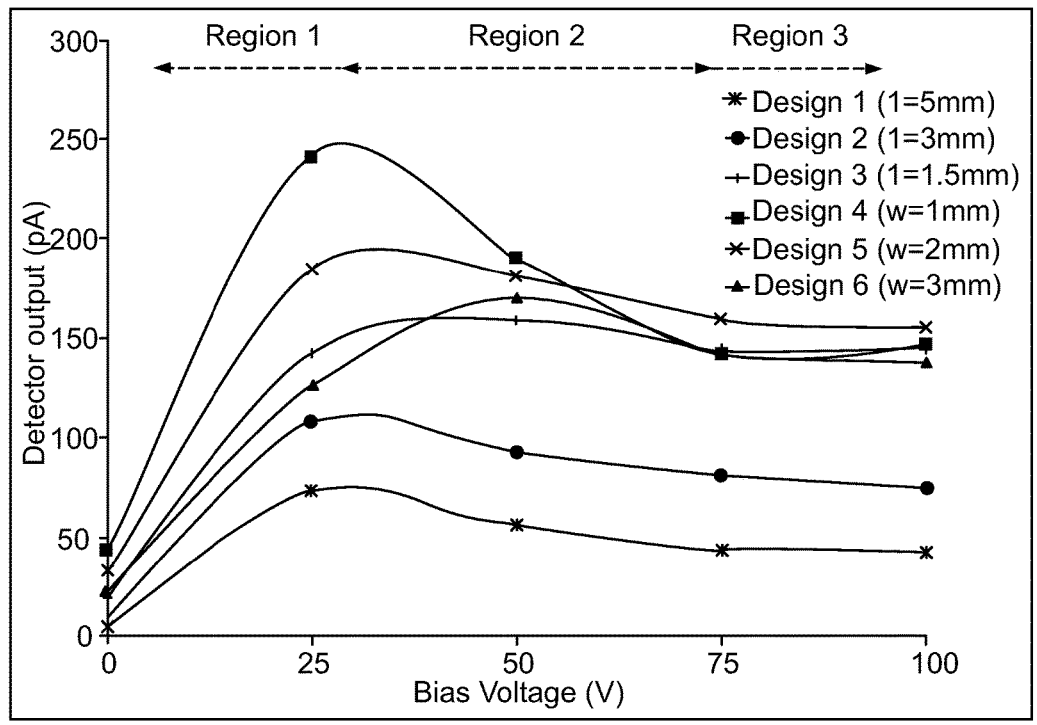
FIG. 12 shows the response of the detector to octane headspace injections from stepped values of bias voltage from 0 to 100 V for an embodiment of the present invention.

The role of bias voltage in actively collecting charged species within collector volume 120 was examined by stepping the voltage from 0 to 100 V in increments of 25 V and measuring the detector response. FIG. 12 also presents the effect of the electrode parameters on the detector response in the presence of a stepped bias voltage. A detector from each previously tested design was tested with the He discharge voltage ($V_p$) set to 550 V. Each data point is the average of two runs. One run was obtained while stepping the voltage up from 0 to 100 V and the other stepping down from 100 to 0 V.

The plot in FIG. 12 can be split into three regions and the behavior of the detector hypothesized as follows. The analytes within the collector volume can be readily ionized by high energy photons and metastable He species from the ionizing flux. In Region 1, in the presence of a small positive bias, negatively charged species from the ionizing flux are collected at the bias electrode, which effectively reduces the possibility of recombination with the positive ions produced from the analytes. Similarly, the electrons created by the soft-ionization of the analytes within the collector volume are collected as well; in effect increasing the time necessary for recombination of the electrons with the ionized analytes. The resultant effect is signal amplification, as noted with the increase in detector output. The sensed current is thus a sum of the effect of the increase in the drift current owing to the removal of the negative species within the volume, and the secondary emission from the impinging flux on the bias. While the former depends on the proximity of the collector electrode to the bias electrode, the latter depends on the proximity of the bias electrode to the He discharge. The slope of the graph, in this region, can be related to the parameter (l+w/2), previously described as the distance of the midpoint of the gap from the He discharge, and tabulated in Table 1.

Beyond a certain voltage, the impact of the bias electrode on repelling positively charged species in the ionizing flux and the collection of high energy electrons reduces the ionization detected within the collector volume. This results in a decrease in detector response, as observed in Region 2, that eventually levels off into Region 3. Assuming that a significant fraction of the ionized analyte species is the result of metastable He atoms, implies that above a certain threshold voltage the energetic primary and secondary electrons responsible for the production of some of the metastable He population are depleted by the bias electrode. This would leave high energy photons produced in the ionizing flux as the primary means of analyte ionization, essentially resulting in a saturated signal since the photon population would be primarily dependent on the He discharge voltage and not the bias voltage. Since, the ionizing flux depends only on the proximity of the bias electrode to the He discharge, the saturated response increases with decreasing values of l but is not affected by w since removal of the electron population significantly reduces the detrimental impact of recombination with analyte ions. This is evident from the similar detector outputs observed in the saturated region (III) for Designs 3-6 with the same value of l=1.5 but varying in w. Measurements were taken with finer resolution in bias voltages between 0 and 50 V. While, the data fit the overall trend of the plot, a relation between the exact voltages of peak response could not be established due to measurement variations associated with such fine voltage resolution measurements.

Figure 13:
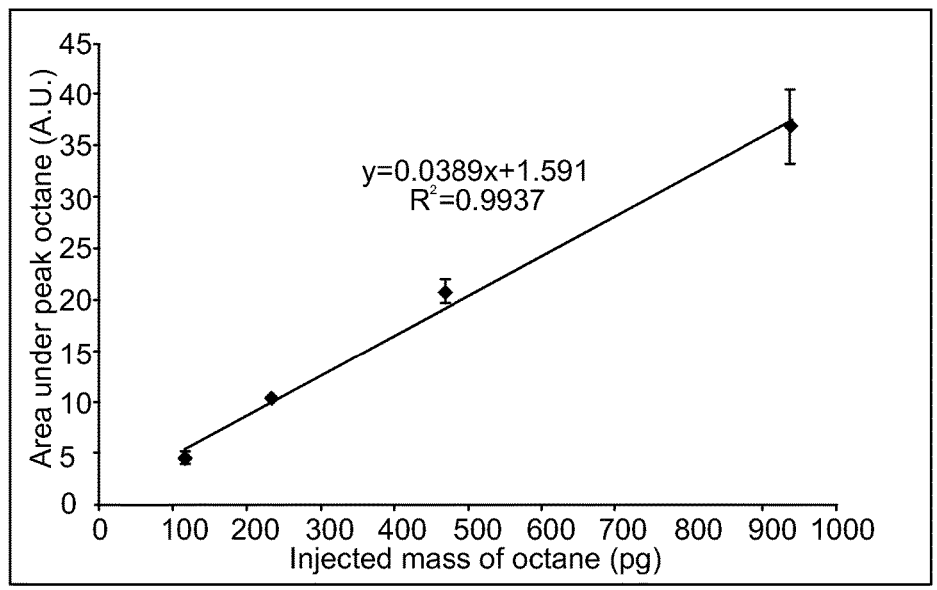
FIG. 13 shows the response of the chip (Design 4) to various injected masses of octane, at a bias voltage of 25 V. Each data point is the average from three successive runs for an embodiment of the present invention.

A sensitivity test for detector 100 in accordance with Design 4 was performed using various dilutions of octane vapor in air. 1 μL samples from mixtures of 25, 50, 100 and 200 μL of octane in 1 L of air were drawn into a gas tight syringe and injected. The discharge voltage was set to 700 V and the bias to 25 V. The power consumption was calculated to be 3.3 mW under these conditions. As shown in FIG. 13, a calibration curve plotting octane peak area against the injected mass exhibited some deviation from linearity at the highest octane mass (950 pg). The worst case deviation in baseline noise from all 9 runs was 2.5 pA. Using a 3/1 signal to noise ratio as the criteria for the absolute limit of detection and plugging into the quadratic fit, an LODl) of 60 pg for octane was obtained.

In another preferred embodiment, the present invention provides an ionization detector having a base having an enclosed chamber. The enclosed chamber has a first end and a second end. The detector also includes a first outlet comprising a source of an excitable medium which may be He. A second outlet is provided which functions a source of an analyte that is transported by a carrier gas, which may be the same as the excitable medium. An ionization source for creating a discharge from the excitable medium is also provided. The embodiment also provides a bias electrode having a terminal end as well as a collector electrode. The ionization source, which may be a pair of electrodes that are spaced apart to form a gap that is 20 μm or less, is disposed between the first end and the bias electrode. The ionizing source has a center or midpoint.

The distance between the bias electrode and midpoint or center of the ionization source forms a first predetermined distance. The collector electrode is disposed between the second end and the bias electrode. The distance between the bias electrode and the collector electrode comprises a second predetermined distance. Also, the gap between the electrodes forms a collector volume or space in which an analyte is ionized by the discharge. In a preferred embodiment, the second outlet is located adjacent the terminal end of the bias electrode. However, in other embodiments, the second outlet may be located in the collector volume or in other locations in between the collector electrode and the ionization source. The collector electrode generates a time dependent current from its interaction with ionized analytes.

The detector may also have a depth of 250 µm and the discharge may be created by 1.4 mW of power. The detector has a minimum limit of detection of 350 pg. The first predetermined distance may be 1.5 mm and the second predetermined distance may be 1 mm.

In yet another preferred embodiment, the detector may have an ionizing source formed by two opposing electrodes that create a gap where the discharge is generated by a voltage of 700 volts, the first predetermined distance may be 1.5 mm, the second predetermined distance may be 1 mm, and the bias electrode may have a voltage of 24 V. The detector may have a power consumption of 3.3 mW and the detector may have a minimum limit of detection of 60 pg. The detector may also have a first predetermined distance that is between 1.5 and 5 mm and a second predetermined distance that is between 1 and 3 mm.

In an additional embodiment, the present invention provides a method of identifying analytes in a carrier gas. The steps of the method comprise flowing analytes in a carrier gas into a detector from an outlet into an enclosed chamber having a first end, a second end, and discharge outlet. The analytes are ionized by interaction with a discharge gas that has been ionized by an ionization source. Analytes are detected by applying a biasing voltage to the bias electrode. The bias electrode has an end positioned at the analyte outlet. Presence of the analyte is determined by generating a time-dependent current based on the interaction of the ionized analytes with the collector electrode. Lastly, the current generated may also be displayed or stored in memory 150 as shown in FIG. 1B.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. An ionization detector comprising:
   a base having an enclosed chamber, said enclosed chamber having an upstream end and a downstream end;
   a channel having an outlet, said outlet comprising a source of an excitable medium and an analyte;
   an ionization source for creating an ionizing discharge from said excitable medium;
   a bias electrode;
   a collector electrode;
   said ionization source having a center that is disposed between said upstream end and said bias electrode, said distance between said bias electrode and said center of said ionizing source comprising a first predetermined distance;
   said collector electrode disposed between said downstream end and said bias electrode, said distance between said bias electrode and said collector electrode comprising a second predetermined distance and defining a collector volume in which the analyte is ionized by said ionizing discharge;
   said channel and outlet extend into said chamber from said upstream end of said chamber;
   said collector electrode generates a current from interaction with the analyte ionized by said ionizing discharge; and
   wherein said ionizing source is formed by two opposing electrodes that create a gap where said ionizing discharge is generated by a voltage of 700 V, said first predetermined distance is 1.5 mm, said second predetermined distance is 1 mm, said bias electrode has a voltage of 24 V, and said detector has minimum limit of detection of 60 pg and a power consumption of 3.3 mW.

2. The detector of claim 1 wherein said chamber has a depth of 250 µm or less.

3. The detector of claim 1 wherein said detector has a power consumption of 1.4 mW or less.

4. The detector of claim 1 wherein said ionizing source is formed by two opposing electrodes that create a gap where said ionizing discharge is generated.

5. The detector of claim 4 wherein said gap is 20 µm or less.

6. The detector of claim 1 wherein said detector has a minimum limit of detection of 350 pg or less.

7. The detector of claim 1 wherein said first predetermined distance is 1.5 mm and said second predetermined distance is 1 mm.

8. The detector of claim 1 wherein said first predetermined distance is between 1.5 and 5 mm and said second predetermined distance is between 1 and 3 mm.

9. The detector of claim 1 wherein said electrodes are planar and said channel outlet, said ionization source, said bias electrode and said collector electrode are all located inside said chamber.

10. The detector of claim 9 wherein said channel and said outlet extend into said chamber from said upstream end of said chamber, said outlet located upstream a spaced distance away from said collector electrode.

11. The detector of claim 9 wherein said channel and said outlet extend into said chamber from said upstream end of said chamber, said outlet located upstream of said bias electrode.

12. The detector of claim 11 wherein said channel outlet is located upstream and proximate to said terminal end of said bias electrode.

13. The detector of claim 12 wherein said base further includes a separation column.

14. An ionization detector comprising:
   a planar base having an enclosed planar chamber, said enclosed chamber having an upstream end and a downstream end;
   said chamber has a depth of 250 µm or less;
   a first channel having a first channel outlet, said first channel outlet comprising a source of an excitable medium;
   a second channel having a second channel outlet, said second channel outlet comprising a source of an analyte;
   an ionization source for creating an ionizing discharge from said excitable medium;
   a planar bias electrode;
   a planar collector electrode;
   said ionization source having a center that is disposed between said upstream end and said bias electrode, said distance between said bias electrode and said center of said ionizing source comprising a first predetermined distance;

said collector electrode disposed between said downstream end and said bias electrode, said distance between said bias electrode and said collector electrode comprising a second predetermined distance and defining a collector volume in which the analyte is ionized by said ionizing discharge;

said second channel and outlet extend into said chamber from said upstream end of said chamber;

said collector electrode generates a current from interaction with the analyte ionized by said ionizing discharge; and wherein said ionizing source is formed by two opposing electrodes that create a gap where said ionizing discharge is generated by a voltage of 700 V, said first predetermined distance is 1.5 mm, said second predetermined distance is 1 mm, said bias electrode has a voltage of 24 V, and said detector has a minimum limit of detection of 60 pg and a power consumption of 3.3 mW.

15. The detector of claim 14 wherein said first channel outlet, said second channel outlet, said ionization source, said bias electrode and said collector electrode are all located inside said chamber.

16. The detector of claim 15 wherein said second channel and said second channel outlet extend into said chamber from said upstream end of said chamber, said second channel outlet located upstream a spaced distance away from said collector electrode.

17. The detector of claim 15 wherein said second channel and said second channel outlet extend into said chamber from said upstream end of said chamber, said second channel outlet located upstream of said bias electrode.

18. The detector of claim 17 wherein said second channel outlet is located upstream and proximate to said terminal end of said bias electrode.

19. The detector of claim 1 wherein said base, said chamber, said bias electrode and said collector electrode are planar.

20. The detector of claim 4 wherein said ionizing discharge is generated by a constant or alternative voltage or a combination of both.

* * * * *